United States Patent [19]

Ferraris et al.

[11] 4,381,381

[45] Apr. 26, 1983

[54] HYDROCARBONACEOUS RESINS, METHOD FOR THEIR PREPARATION AND MEANS THEREFOR

[75] Inventors: Giuseppe Ferraris; Sebastiano Cesca, both of San Donato Milanese, Italy

[73] Assignee: Anic S.p.A., Palermo, Italy

[21] Appl. No.: 197,206

[22] Filed: Oct. 15, 1980

Related U.S. Application Data

[63] Continuation of Ser. No. 16,431, Mar. 1, 1979, abandoned.

[30] Foreign Application Priority Data

Apr. 12, 1978 [IT] Italy .............................. 22219 A/78

[51] Int. Cl.$^3$ ......................... C08F 2/00; C08F 110/00
[52] U.S. Cl. ...................................... 526/75; 526/226; 526/237; 526/290
[58] Field of Search ................. 526/75, 226, 237, 290

[56] References Cited

U.S. PATENT DOCUMENTS

| | | | |
|---|---|---|---|
| 2,753,325 | 7/1956 | Banes ................................... | 526/290 |
| 2,849,512 | 8/1958 | Banes et al. ......................... | 526/290 |
| 2,946,775 | 7/1960 | de Vries et al. .................... | 526/290 |
| 3,014,012 | 12/1961 | Riley et al. ........................... | 526/290 |
| 3,784,530 | 1/1974 | Osborn et al. ....................... | 526/290 |
| 3,813,357 | 5/1974 | St. Cyr ................................. | 526/290 |
| 4,038,346 | 7/1977 | Feeney ................................. | 526/290 |

*Primary Examiner*—Harry Wong, Jr.
*Attorney, Agent, or Firm*—Morgan, Finnegan, Pine, Foley & Lee

[57] ABSTRACT

A process for preparing hydrocarbonaceous resins from $C_5$ fractions is disclosed in which the starting hydrocarbonaceous fraction is enriched with cis-piperylene. A catalyst system is also disclosed for the formation of the resins by polymerization and the simplest catalyst is an aluminum halide. In other embodiments, the aluminum halide is used together with a second component such as a hydrocarbyl halide and/or a halide of a metal selected from Sn, Si, B, Ti, Pb, Sb, As and others. Resins having improved physico-chemical properties are obtained.

14 Claims, 1 Drawing Figure

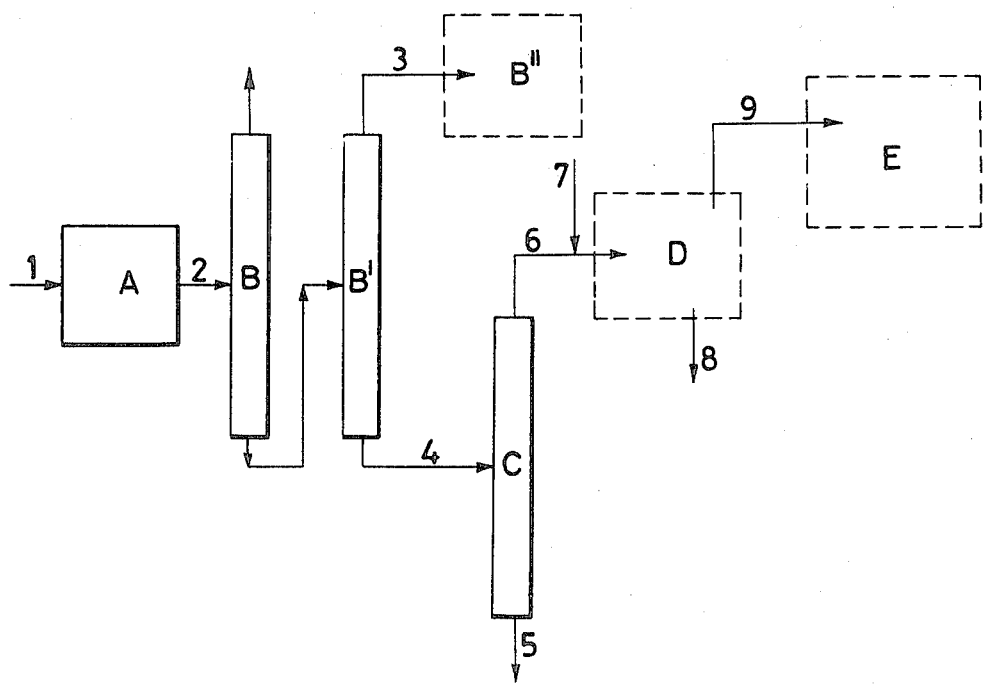

HYDROCARBONACEOUS RESINS, METHOD FOR THEIR PREPARATION AND MEANS THEREFOR

This is a continuation, of application Ser. No. 016,431 filed Mar. 1, 1979 and now abandoned.

BACKGROUND OF THE INVENTION

This invention relates to novel hydrocarbonaceous resins in which the starting hydrocarbon fraction, $C_5$, employed is enriched with cis-piperylene and also to a method for their preparation and also to means adapted for such preparation.

It is known that it is possible to obtain hydrocarbonaceous fractions of a composition which varies according to the operative conditions of the steam-cracker in petroleum crushing processes. One of such fractions is composed of $C_5$ hydrocarbons and it is known that such fraction can be used as such, or also after treatments such as dimerization, fractionation and the like, in the preparation of hydrocarbonaceous resins by employing Friedel-Crafts catalysts. Such $C_5$ hydrocarbon fraction contains diolefines such as isoprene, piperylene and mono-cyclopentadiene, olefines such as 2-methyl-1-butene, 2-methyl-2-butene, pentenes, cyclopentene and saturated hydrocarbons such as cyclopentane, nor.pentane and others.

The percentage of these components in the fraction varies, of course, according to the type of charge present in the steam-cracker and the more or less drastic cracking conditions.

A first object of the present invention is to employ the $C_5$ fraction in the preparation of the hydrocarbonaceous resins, the characteristic of which, as mentioned above, is a high content of cis-piperylene. This fraction is obtained by subjecting the $C_5$ hydrocarbon fraction to a particular treatment which is an integral part of the present invention and of which an exemplary diagram is given in order to make the several steps of the same clearly understood. In the drawing accompanying the present specification the block-diagram shows the several steps to be followed in order to obtain the $C_5$ fraction mentioned above. In the diagram a suggestion is also given as to the subsequent polymerization reaction. By so doing, however it is not intended, as is obvious, that the final formation of the resin is bound to the method followed for the production of the starting composition. On the contrary, the polymerization reaction can be performed irrespective of the origin of the composition employed, provided that it has a high content of cis piperylene.

The purpose of the accompanying drawing is to illustrate the method of the invention including the preliminary preparation of the $C_5$ fraction of interest, it being reiterated that such preparation can be effected according to any procedure which is considered appropriate by a skilled technician.

Referring now to the diagram shown in the drawing, the hydrocarbonaceous fraction 1, exiting the steam-cracker, is fed to a dimerizer A, in which monocyclopentadiene (CPD) is converted into its dimer, dicyclopentadiene (DCP).

At the exit from the dimerizer A, the average composition of the hydrocarbon fraction $C_5$, 2, is comprised of the following constituents in the stated ranges:

|  | % by wt |
| --- | --- |
| Isoprene | 15–23 |
| Piperylene-trans | 9.5–10.5 |
| Piperylene-cis | 5–6.5 |
| CPD | 0.5–1.0 |
| DCP | 15–20 |

The balance is saturated hydrocarbons and $C_5$ olefines.

The fraction, 2, is sent to two distillation columns, B and B', in which separation by rectification is effected in B for the lighter components, and in B' for the heavier ones, such as the piperylenes and DCP. The fraction, 3, which is enriched with isoprene, is sent to isoprene recovery at B" by following the procedures disclosed in the U.S. Pat. No. 3,851,010 assigned to SNAM-PROGETTI SpA and in the article by A. Ginnasi, G. Paret and C. Rescalli, "The Recovery of isoprene from pyrolysis gasoline", presented at the Symposium on Olefine Production, Bratislava, 4 to 9 September 1972.

The tail hydrocarbon fraction, 4, of the column B' has an average composition comprised of the following constituents in the stated ranges:

|  | % by wt |
| --- | --- |
| Isoprene | 0.4–4 |
| Piperylene-trans | 19.5–23.5 |
| Piperylene-cis | 12.5–15.0 |
| CPD | 04–1.0 |
| DCP | 34.5–45.5 |

The balance is saturated hydrocarbons and $C_5$ olefines.

The fraction, 4, is then sent to the rectification column C, from the bottom of which the heavier fraction, 5 is separated, which contains DCP in a percentage of 85% and over.

The head fraction, 6, of the column C contains a high percentages of piperylenes and its composition varies within the following ranges:

|  | % by wt |
| --- | --- |
| Isoprene | 1–6 |
| Piperylene-trans & cis | 40–70 |
| CPD | 0.8–1.5 |
| DCP | less than 0.5 |

The balance is saturated hydrocarbons and $C_5$ olefines.

Such fraction, 6, is subsequently added to butadiene, 7, and the mixture is sent to the polymerization reaction for copolymerization to butadiene-piperylene(trans), D, for example, by using the procedures disclosed in A. Carbonaro, V. Zamboni, G. Novajra, G. Dall'Asta, Rubb. Chem. & Technol., 46, 1274 (1973). According to what has been reported in that paper, the butadiene-piperylene-trans copolymer, 8, is obtained in a yield of over 80% referred to the starting piperylene-trans, whereas the cis-isomer remains unaltered. On completion of the copolymerization run, after the separation of the polymer, 8, and the recovery of the unreacted butadiene and the reaction solvent, a hydrocarbonaceous fraction $C_5$ is obtained, which is enriched with piperylene-cis, 9, and it is this fraction which is the raw material for the preparation of hydrocarbonaceous resins according to the present invention. A typical but non-limiting composition of the fraction 9 is as follows:

| | |
|---|---|
| Isoprene | 7% by wt |
| Piperylene | 9 |
| Piperylene-cis | 22 |
| DCP | less than 0.1 | the remainder being saturated hydrocarbons and $C_5$ olefines.

The percentages of the several components of the fractions vary, at any rate, not only as a function of the feed in the copolymerization stage, but also as a function of the operating conditions of the polymerization reaction itself.

The fraction 9, is then sent to the resin-formation step E which is carried out in the presence of cationic catalysts, examples of which will be given hereinafter.

It is also known in the patent literature that it is possible to vary the softening point of the $C_5$ hydrocarbonaceous resins by adding to the starting $C_5$ fraction other hydrocarbonaceous fractions or pure monomers or mixtures of pure monomers.

The objective is to obtain products which have physicochemical properties which cover a wide field of application in the adhesive range.

In this connection, it has been observed by the Applicants that it is possible, starting from the hydrocarbonaceous fraction 9 mentioned above, and by addition thereto of cyclic monomers such as dicyclopentadiene (DCP), 4-vinyl-1-cyclohexene (VCE), styrene or its derivatives or $C_8$–$C_9$ hydrocarbonaceous fractions, to obtain, by polymerization, resins having a softening point which is higher than that exhibits by the resins which can be obtained from the 9 fraction as such.

As a matter of fact, when operating with all the other conditions being the same but with percentages of such monomers varying between 20% and 120% by weight relative to the hydrocarbonaceous fraction 9, resins are obtained, which have a softening point, on an average, above 90° C. On the other hand, by adding to the fraction 9 in the same ratios indicated above, oligomers obtained by polymerizing propylene to trimers, tetramers, pentamers or hydrocarbon fractions $C_4$ stripped of butadiene, there are obtained products which have a lower softening point which is below 50° C. and under certain conditions below room temperature.

BRIEF STATEMENT OF THE INVENTION

According to the present invention it is thus possible to obtain hydrocarbonaceous resins which are adapted to use as pressure-sensitive adhesives, hot-melt adhesives, sealants and so forth, by polymerization reactions of $C_5$ hydrocarbon fractions which have been enriched with piperylene-cis, both as such and in admixture with DCP, VCE, styrene and its derivatives, hydrocarbonaceous fractions $C_8$–$C_9$, tetramers of propylene and butadienestripped $C_4$ fractions.

According to a first embodiment of the present invention the polymerization reaction is carried out in the presence of a catalyst comprising an aluminum halide of the formula $AlX_3$ wherein X is a halogen atom and the reaction takes place in an aromatic solvent or an aliphatic halogen-substituted hydrocarbon having from 1 to 12 carbon atoms, at a temperature in the range of from $-10°$ C. to $+120°$ C. In addition, the reaction takes place in a heterogeneous phase since the aluminum halide is used in the form of a suspension which is finely subdivided in the reaction solvent.

The products which are obtained from such polymerization have an average molecular weight of from 700 to 5,000 and contain unsaturations which can be expressed in terms of iodine number (grams of $I_2$ absorbed by 100 g of polymer) which is determined according to a number of methods including ASTM D 1959-69. They have, moreover, a softening point between $+50°$ C., and $+140°$ C., as determined with the method of melting point determination in an open capillary tube.

As an alternative, the conversion into resin of the $C_5$ fraction, according to another aspect of this invention, can be achieved by using another catalytic system, in which the aluminum halide is no longer employed as such, but rather in union with a second component. More particularly, the system is composed of two components selected from among the following classes of compounds:

(a) an aluminum halide of the formula $AlX_3$ wherein X is a halogen atom, and
(b) a compound capable of reacting with the halides of the class indicated above to give the catalytic species capable of starting polymerization and selected from among those belonging to one of the following classes:
 (I) compounds corresponding to the general formula:

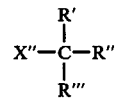

wherein X″ is a halogen, R′, R″ and R‴ are hydrogen atoms or alkyl or aryl radicals, equal to or different from each other, and containing from 1 to 12 carbon atoms, the case being excluded where all three R′, R″ and R‴ are hydrogen simultaneously; and
(II) Metal halides of the general formula:

wherein X‴ is a halogen, Y′ is an oxygen or a sulfur atom, Me is a metal selected from among Sn, Si, B, Ti, Pb, Sb, As, Bi, Mg and V, m is an integer which can also be zero, n is an integer and the sum $2m+n$ is equal to the valency of the metal concerned.

DESCRIPTION OF THE PREFERRED EMBODIMENT

Examples of aluminum halides which can be used are $AlCl_3$, $AlBr_3$ and $AlI_3$, whereas compounds of the class (b) are tert.butyl chloride, isopropyl chloride, benzyl chloride, isopropyl bromide, tert.butyl bromide for subclass I, and $SnCl_4$, $SiCl_4$, $BCl_3$, $TiCl_4$, $PbCl_4$, $SbCl_5$, $AsCl_5$ and others for subclass II. The two components of the catalytic system can be introduced in the reaction medium simultaneously, or it is possible to introduce them discretely and the order of the addition has no bearing whatsoever on the catalytic species which results. The molar ratio component (a) to component (b) can range between 0.1 and 5 to 1 and the preferred range is between from 0.5 and 2 to 1.

The solvents employed in the polymerization, the working conditions, the reaction temperatures are the same as mentioned above.

The products obtained in this way have physico-chemical properties which are equivalent to those of the previous products.

It has been found, in addition, and this is another aspect of the present invention, that a process for converting the $C_5$ hydrocarbonaceous fraction aforesaid into resin can use catalytic systems other than those described hereinabove and thus the resinification may be achieved in a homogeneous phase.

Such catalytic systems can be selected from among the following classes of compounds:

(I) an organic metallic compound of aluminum which is represented by the following general formula:

$R_m AlX_{3-m}$ wherein X is a halogen atom, R is hydrogen or a monovalent alkyl, aryl, cycloalkyl, aralkyl, alkaryl, alcoxy or ester radical having from 1 to 12 carbon atoms and m is a number from 1 to 3; and (II) a system composed of two components selected from among the following classes of compounds:
(a) a metallic organic compound of aluminum represented by the following general formula:

$R_m AlX_{3-m}$ wherein X is a halogen atom, R is hydrogen or a monovalent alkyl, aryl, cycloalkyl, aralkyl, alkaryl, alcoxy ester radical having from 1 to 12 carbon atoms and m is a number between 1 and 3; and (b) a compound capable of reacting with the compounds of (a) class to give a catalytic species capable of starting polymerization and selected from among those belonging to one of the following classes:
(i) halogens or interhalogenic compounds of the general formula X'Y, wherein X' and Y are the same or different are selected from among chlorine, bromine, iodine and fluorine,
(ii) compounds corresponding to the general formula:

wherein X" is a halogen, R', R" and R'" are hydrogen atoms or alkyl or aryl radicals which may be the same or different from each other and which contain from 1 to 12 carbon atoms, but all cannot be hydrogen simultaneously,
(iii) metal halides of the general formula:

$MeX_n'''Y_m'$ wherein X'" is a halogen, Y' is an oxygen atom or a sulfur atom, Me is a metallic element selected from among Sn, Si, B, Ti, Pb, Sb, As, Bi, Mg and V, m is an integer which can also be zero, n is an integer and the sum 2m+n is equal to the valency of the metal concerned,
(iv) a compound capable of reacting with the compounds of the class (a) to give a catalytic species capable of starting the polymerization and having the formula HX wherein X is a halogen.

Examples of compounds belonging to the class (a) are $AlEtCl_2$, $AlEt_{1.5}Cl_{1.5}$, $AlEtBr_2$, $AlEt_2Cl$, $AlEt_3$, Al(isopropyl)$_3$, Al(isobutyl)$_3$ and others.

Examples of compounds belonging to the class (b) are $Cl_2$, $Br_2$, $I_2$, ICl, IBr, $F_2$ for subclass (i), and tert. butyl chloride, isopropyl, chloride, benzyl chloride, isopropyl bromide, tert.butyl bromide for subclass (ii), and $SnCl_4$, $SiCl_4$, $BCl_3$, $TiCl_4$, $PbCl_4$, $SbCl_5$, $AsCl_5$ and others for subclass (iii), and HCl, HBr, HF and HI for subclass N.

The two components of the catalytic system can be introduced in the reaction medium simultaneously, or it is possible to introduce the two components discretely and the order of the introduction does not influence in any manner the catalytic species which results the molar ratio of component (a) to component (b) can range between 0.1 and 5 to 1 and the preferred range is between from 0.5 and 2 to 1.

Another useful catalytic system (III) composed of a liquid complex of Al halide, aromatic hydrocarbon and alkyl halide in relative ratios of 1:2 to 3:2–3 as prepared according to the disclosure of the German Pat. No. 1,915,224 may also be used in the practice of the present invention.

The solvents used in the polymerization and the reaction temperatures are the same as set forth above.

The products so obtained according to the described procedures have physico-chemical properties akin to those of the previously mentioned products.

THE EXAMPLES

All that which has been set forth above and the practical procedures will become clearer from a scrutiny of the following illustrative Examples which are not to be considered limitations of the invention.

EXAMPLE 1

A steel autoclave having a volume of 100 mls, equipped with a magnetic stirrer and a thermometer-well and which has been previously dried under vacuum is charged with a slurry composed of 5 mls of toluene and 1.3 millimol of $AlCl_3$.

The temperature is stabilized to +60° C. 53 g of the hydrocarbonaceous fraction 9 of (FIG. 1) one introduced with the aid of nitrogen superpressure.

A temperature rise to 66° C. is experienced. The reaction is continued for 45 minutes after which it is stopped by the addition of methanol. The temperature is brought to 20° C. and the resultant polymeric solution is coagulated with methanol. The polymer is separated and dried under vacuum (rotary pump) overnight. There are obtained 19.8 g of a product having a mol wt(averageosmometric), $\overline{Mn}=2200$, a content of unsaturations, expressed in terms of iodine number, of 170, when determined with the ASTM D-1959-69 method, and a softening point of 60° C. calculated according to the method of determining melting point in an open capillary tube.

EXAMPLE 2

Using the same procedure as in Example 1, the autoclave is charged with the same amounts of solvent, catalyst and fraction 9, the only exception being that the solvent used for slurrying the $AlCl_3$ is $CH_2Cl_2$. The reaction is carried out under the same conditions as to temperature and time as reported for Example 1.

There are obtained 20.6 g of a dry product which has an $\overline{M}n=2300$, an iodine number of 164 and a softening point of 84° C.

EXAMPLE 3

Repeating again the procedure of Example 1, there are introduced in the autoclave a slurry of 1.4 millimol of AlCl$_3$ in 5 mls of toluene. The temperature is stabilized to +60° C. and there are introduced with a nitrogen overpressure, 53 g of the hydrocarbon fraction 9 (see FIG. 1) together with 1.3 millimol of tert.butyl chloride. A temperature rise to 68° C. is experienced and the reaction is allowed to proceed for 45 minutes. After stopping the reaction with methanol and coagulation and drying of the polymer, there are obtained 25.2 g of a dry product having an $\overline{M}n$ of 2200, an iodine number of 165 and a softening point of 66° C.

EXAMPLE 4

Using the same procedure as in Example 3 the autoclave is charged with the same amounts of AlCl$_3$, toluene, fraction 9 and cocatalyst, the only exception being that the latter is SnCl$_4$. The reaction is carried out at the same temperature and for the same time as in Example 3. There are obtained, after discontinuation of the reaction and recovery of the polymer, 23.3 g of a dry product having an $\overline{M}n$ of 2100, an iodine number of 173 and a softening point of 62° C.

EXAMPLE 5

Repeating the procedure of Example 1, the autoclave is charged with 10.5 g of the hydrocarbon fraction 9 (see FIG. 1). The temperature is stabilized to 20° C. and the polymerization is primed by adding, under a nitrogen overpressure, 0.5 millimol of AlEtCl$_2$ dissolved in 1 ml of toluene. A temperature rise to 24° C. is observed. The reaction is allowed to proceed for 45 mins. The polymerization is discontinued by adding a few mls of methanol and the polymer solution is coagulated in methanol. The polymer is recovered and dried under vacuum (rotary pump) overnight. There are obtained 4.65 g of a dry product having an $\overline{M}n$ of 2400, an iodine number of 189 and a softening point of 57° C.

EXAMPLE 6

Using the same procedure as in Example 1, the autoclave is charged with 10.5 g of the hydrocarbon fraction 9 along with 0.5 millimol of Cl$_2$ diluted in 1 ml of toluene. The temperature is stabilized at 20° C. and the reaction is started by the addition of 0.5 millimol of AlEtCl$_2$ dissolved in 1 ml of toluene. A temperature rise to 27° C. is experienced and the reaction is allowed to proceed for 45 minutes. On completion of the reaction and recovery of the polymer, there are obtained 5.85 g of a dry product having an $\overline{M}n$ of 2000, an iodine number of 152 and a softening point of 67° C.

EXAMPLE 7

Again employing the same procedure as in Example 1, the autoclave is charged with 10.5 g of the hydrocarbon fraction 9 and 0.5 millimol of tert.butyl chloride diluted in 1 ml of toluene. The temperature is stabilized to 20° C. and the reaction is primed by the addition of 0.5 millimol of AlEtCl$_2$ diluted in 1 ml of toluene. A temperature rise to 28° C. is experienced and the reaction is allowed to proceed for 45 minutes. On completion of the reaction and recovery of the polymer, there are obtained 5.90 g of a dry product having an $\overline{M}n$ of 2200, an iodine number of 155 and a softening point of 63° C.

EXAMPLE 8

Again repeating the procedure as in Example 1, the autoclave is charged with 10.5 g of the hydrocarbon fraction 9 and 0.5 millimol of SnCl$_4$ diluted in 1 ml of toluene. The temperature is stabilized to 20° C. and the reaction is primed by introducing 0.5 millimol of AlEtCl$_2$ diluted in 1 ml of toluene. A rise of the temperature to 29° C. is experienced and the reaction is allowed to proceed for 45 minutes. The reaction is stopped with methanol and the polymer is recovered. There are obtained 6.0 g of a dry product having an $\overline{M}n$ of 1800, an iodine number of 157 and a softening point of 65° C.

EXAMPLE 9

Using again the same procedure as employed in Example 1, the autoclave is charged with 10.5 g of the hydrocarbon fraction 9 and 0.5 millimol of HCl diluted in 1 ml of toluene. The temperature is stabilized to 20° C. and the reaction is primed by introducing 0.5 millimol of AlEtCl$_2$ diluted in 1 ml of toluene. A temperature rise to 25° C. is experienced and the reaction is allowed to proceed for 45 minutes. On termination of the reaction and recovery of the polymer, there are obtained 5.75 g of a dry product having an $\overline{M}n$ of 1880, an iodine number of 169 and a softening point of 63° C.

EXAMPLE 10

Again repeating the same procedure as for Example 1, the autoclave is charged with 0.55 ml (corresponding to 1.3 millimol as AlCl$_3$), of a liquid ternary complex AlCl$_3$-tolueneethyl chloride (prepared according to the disclosure in the German Patent 1,915,224 of Oct. 2, 1969) and 5 mls of toluene. The temperature is stabilized to +60° C. and there are introduced, by nitrogen overpressure, 53 g of the hydrocarbon fraction 9. A temperature rise to 66° C. is observed and the reaction is allowed to proceed for 45 minutes. On termination of the reaction and recovery of the polymer, there are obtained 21.4 g of a dry product having an $\overline{M}n$ of 2150, an iodine number of 171 and a softening point of 64° C.

EXAMPLE 11

Using again the same procedure as reported in Example 1, the autoclave is charged with 17.5 g of the hydrocarbon fraction 9, 17.5 g of DCP and 1.0 millimol of tert. butyl chloride. The temperature is stabilized to 20° C. and the reaction is started by introducing 1.0 millimol of AlEtCl$_2$ diluted in 1 ml of toluene. It is observed that the temperature rises to 24° C. and the reaction is allowed to proceed for 60 minutes. Upon termination of the reaction and recovery of the polymer, there are obtained 12.1 g of a dry product exhibiting an $\overline{M}n$ of 1590, an iodine number of 210 and a softening point of 100° C.

EXAMPLE 12

Using the same procedure as in Example 1, the autoclave is charged with 2.0 millimols of AlCl$_3$ slurried in 3 mls of toluene. The temperature is stabilized to 20° C. and there is added, by nitrogen overpressure, a mixture composed of 10.5 g of the hydrocarbon fraction 9 and 10.5 g of 4-vinyl-1-cyclohexene. A temperature rise to 28° C. is observed and the reaction is allowed to proceed for 45 minutes. Upon termination of the reaction and recovery of the polymer, there are obtained 6.2 g of a dry product having an $\overline{Mn}$ of 3700, an iodine number of 177 and a softening point of 108° C.

EXAMPLE 13

Again using the same procedure as set forth in Example 1, the autoclave is charged with 0.5 millimol of AlCl$_3$ slurried in 1 ml of toluene. The temperature is stabilized to 20° C. and there is introduced a mixture consisting of 10.5 g of the hydrocarbon fraction 9 and 3.9 g of styrene. It is observed that the temperature rises to 27° C. and the reaction is allowed to proceed for 45 minutes. Upon termination of the reaction and recovery of the polymer, there are obtained 7.2 g of dry product having an $\overline{Mn}$ of 2230, an iodine number of 135 and a softening point of 91° C.

EXAMPLE 14

Once again using the same procedure as in Example 1, the autoclave is charged with 1.6 millimol of AlCl$_3$ and 4 mls of CH$_2$Cl$_2$. The temperature is stabilized to +100° C. and a mixture is introduced which consists of 42 g of the hydrocarbon fraction 9 and 12.5 g of low oligomers of propylene (trimers, tetramers and pentamers).

It is observed that the temperature rises to 104° C. and the reaction is allowed to proceed for 60 minutes. Upon termination of the reaction and recovery of the polymer there are obtained 9.2 g of a dry product having an $\overline{Mn}$ of 500, an iodine number of 158 and a softening point below 20° C.

We claim:

1. A process for the preparation of hydrocarbonaceous resins from C$_5$ hydrocarbon fractions containing at least 22% by weight of cis-piperylene comprising passing a hydrocarbonaceous fraction exiting a steam-cracker to a dimerizer and subsequently to a plurality of distillation columns, separating said hydrocarbonaceous fraction into light components and heavy components, passing said heavy components through a rectification column, recovering as heads a fraction containing a high percentage of cis-piperylene and trans-piperylene, introducing the heads fraction into a polymerization reactor with butadiene and forming a copolymer of butadiene and transpiperylene, removing said copolymer and unreacted butadiene from the polymerization reaction and obtaining a C$_5$ hydrocarbon fraction enriched with at least 22% by weight of cis-piperylene, polymerizing the enriched C$_5$ hydrocarbon fraction in the presence of a catalyst selected from an aluminum halide of the formula AlX$_3$, wherein X is a halogen atom or an organic metallic compound of aluminum having the general formula:

$$R_m AlX_{3-m}$$

wherein X is a halogen atom, R is hydrogen or a monovalent alkyl, aryl, cycloalkyl, aralkyl, alkaryl, alkoxy or ester radical having from 1 to 12 carbon atoms and m is a number from 1 and 3, in a solvent selected from the group consisting of aromatic hydrocarbon solvents and aliphatic, halogen-substituted hydrocarbon solvents containing from 1 to 12 carbon atoms and obtaining a hydrocarbonaceous resin adhesive enriched with cis-piperylene having a softening point from below 20° C. up to 140° C.

2. A process according to claim 1 wherein the catalyst includes a second component which is capable of reacting with the halide of the formula AlX$_3$ or the organic metallic compound of aluminum to give a catalyst species capable of starting the polymerization and which is selected from the group consisting of (i) halogen compounds of the general formula, X'Y, wherein X' and Y are the same or different and are selected from the group consisting of chlorine, bromine, iodine and fluorine;

(ii) compounds having the general formula,

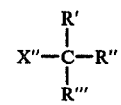

wherein X" is a halogen, R', R" and R'" are hydrogen atoms or alkyl or aryl radicals containing from 1 to 12 carbon atoms and which can be the same or different from each other and cannot be all hydrogen simultaneously;

(iii) metallic halides having the general formula, $$MeX_n''' Y'_m$$

wherein X''' is a halogen, Y' is oxygen or sulfur, Me is a metallic element selected from the group consisting of Sn, Si, B, Ti, Pb, Sb, As, Bi, Mg and V, m is an integer including zero, n is an integer and the sum 2m+n equals the valence of Me; and (iv) compounds having the general formula, HX, wherein X is a halogen.

3. A process according to claim 1 wherein the catalyst comprises a system which is a liquid complex including the aluminum halide, AlX$_3$, an aromatic hydrocarbon solvent and alkyl halide having the general formula,

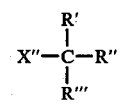

wherein X" is a halogen and R', R" and R'" are alkyl radicals which may be the same or different and which contain from 1 to 12 carbon atoms, and said aluminum halide, said solvent and said alkyl halide are present in the relative ratios of 1:2-3:2-3.

4. A process according to claim 1 wherein the polymerization is carried out at a temperature which can be varied from −10° C. to +120° C.

5. A process according to claim 1 wherein the catalyst is AlCl$_3$.

6. A process according to claim 1 wherein the catalyst is AlEtCl$_2$.

7. A process according to claim 2 wherein the catalyst comprises AlCl$_3$ and SnCl$_4$.

8. A process according to claim 2 wherein the catalyst comprises Cl$_2$ and AlEt$_2$.

9. A process according to claim 2 wherein the catalyst comprises tertiary-butyl chloride and AlEtCl$_2$.

10. A process according to claim 2 wherein the catalyst comprises SnCl$_4$ and AlEtCl$_2$.

11. A process according to claim 2 wherein the catalyst comprises HCl and AlEtCl$_2$.

12. A process according to claim 2 wherein the catalyst comprises AlCl$_3$ and ethyl chloride.

13. A process according to claim 2 wherein the catalyst comprises tertiary butylchloride and the C$_5$ hydrocarbon fraction is copolymerized with di-cyclopentadiene.

14. A process according to claim 2 wherein the catalyst comprises AlCl$_3$ and the C$_5$ hydrocarbon fraction is copolymerized with 4-vinyl-1-cyclohexene.

* * * * *